(12) United States Patent
Locke et al.

(10) Patent No.: US 9,408,941 B2
(45) Date of Patent: Aug. 9, 2016

(54) TISSUE TREATMENT SYSTEMS AND METHODS HAVING A NON-TACTILE-STIMULUS-ACTIVATED, MACROSCOPICALLY-DEFORMING MATERIAL

(75) Inventors: Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 943 days.

(21) Appl. No.: 13/559,307

(22) Filed: Jul. 26, 2012

(65) Prior Publication Data

US 2013/0072850 A1    Mar. 21, 2013

Related U.S. Application Data

(60) Provisional application No. 61/536,981, filed on Sep. 20, 2011.

(51) Int. Cl.
*A61L 15/42* (2006.01)
*A61L 15/22* (2006.01)

(52) U.S. Cl.
CPC .............. *A61L 15/42* (2013.01); *A61L 15/22* (2013.01); *A61L 2400/16* (2013.01)

(58) Field of Classification Search
CPC ...... A61L 15/22; A61L 15/42; A61L 2400/16
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Search Report and Written Opinion for corresponding PCT/US2012/048370, mailed Nov. 7, 2012.

(Continued)

*Primary Examiner* — Leslie Deak
*Assistant Examiner* — Kai Weng

(57) ABSTRACT

A system for treating a tissue site of a patient includes a dressing filler adapted to be positioned at the tissue site. The dressing filler includes a base and a plurality of nodes extending from the base. The base further includes a plurality of openings disposed in the base. At least one of the plurality of nodes is comprised of a non-tactile-stimulus-activated, macroscopically-deforming (NTSAMD) material.

27 Claims, 9 Drawing Sheets

(56) References Cited

U.S. PATENT DOCUMENTS

| | | |
|---|---|---|
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0085693 A1* | 4/2005 | Belson et al. ............ 600/146 |
| 2008/0275409 A1 | 11/2008 | Kane et al. |
| 2010/0160876 A1 | 6/2010 | Robinson et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO 2010/053870 A1 | 5/2010 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

(56) References Cited

OTHER PUBLICATIONS

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ð ukić, Ž. Maksimović, Ð.. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

\* cited by examiner

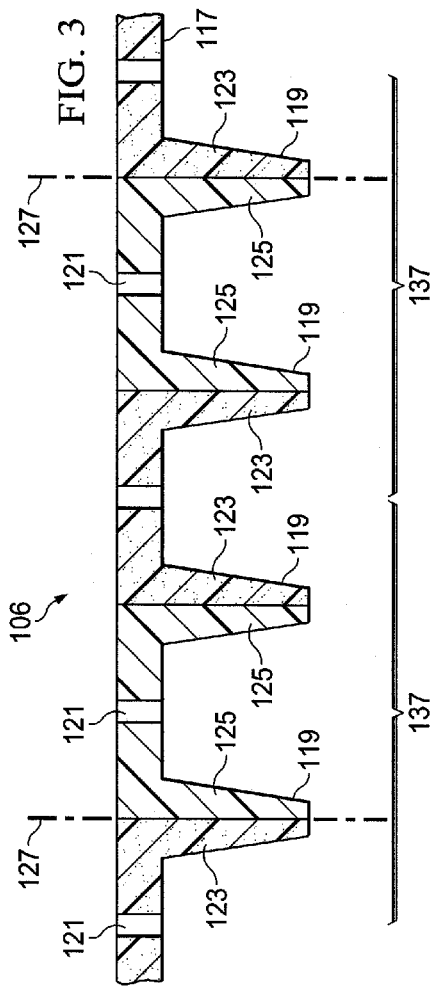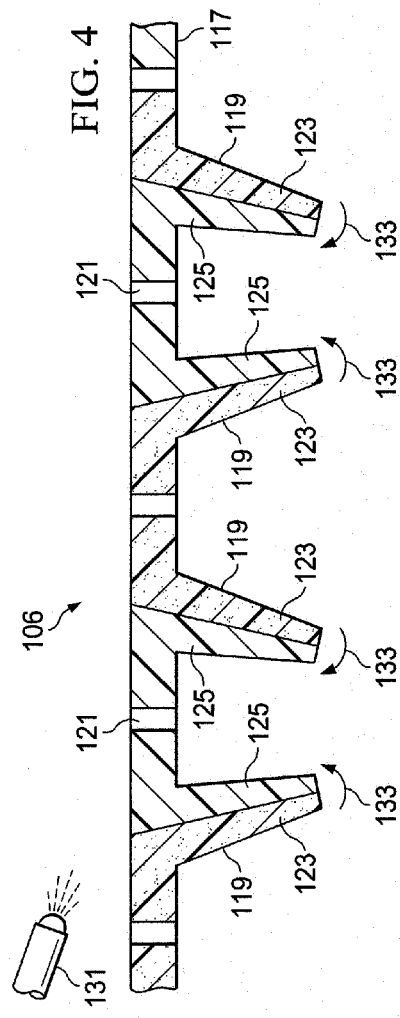

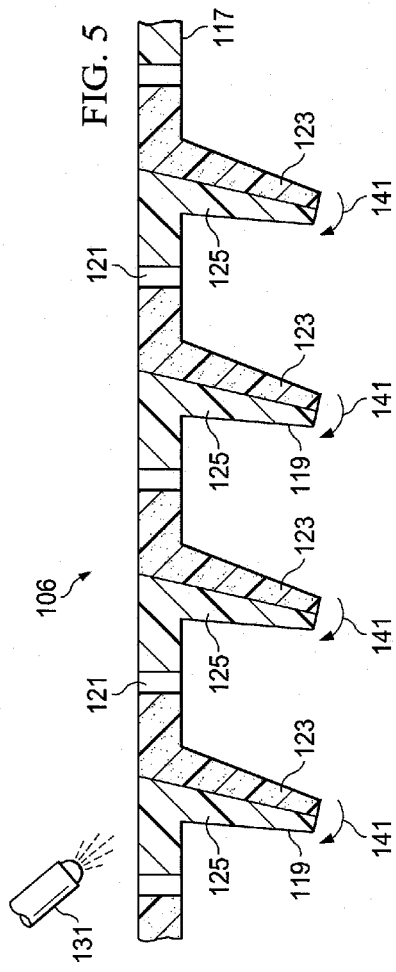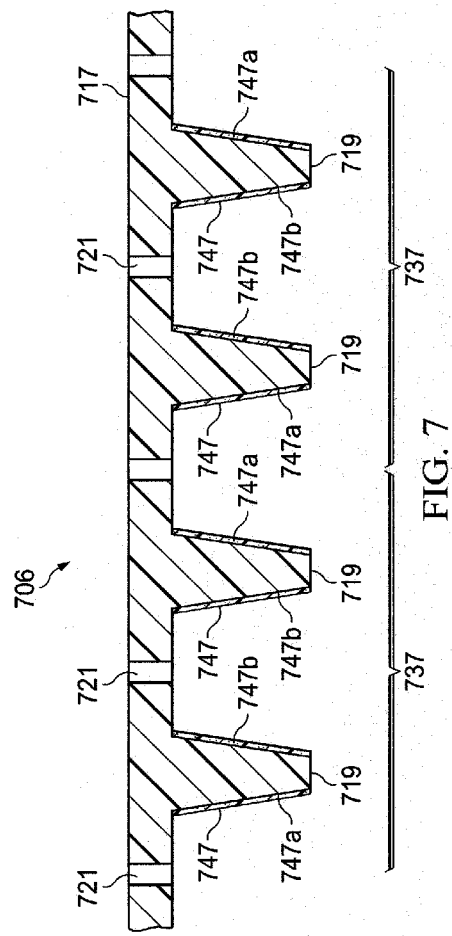

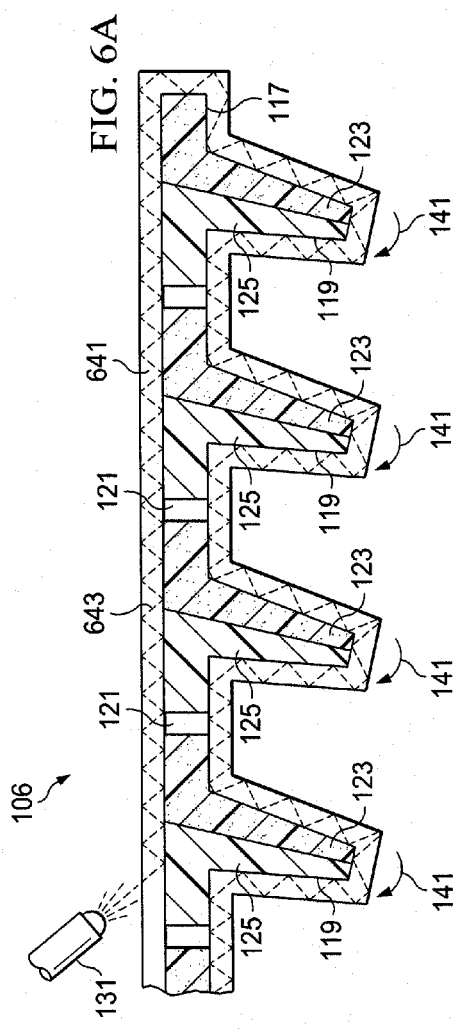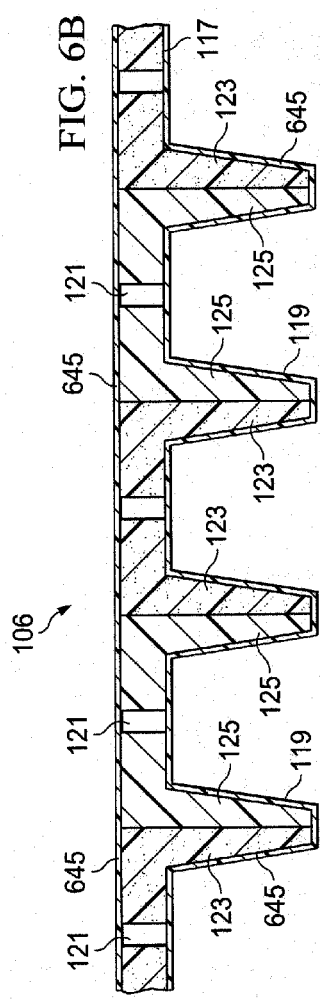

TISSUE TREATMENT SYSTEMS AND METHODS HAVING A NON-TACTILE-STIMULUS-ACTIVATED, MACROSCOPICALLY-DEFORMING MATERIAL

RELATED APPLICATIONS

The present invention claims the benefit, under 35 USC §119(e), of the filing of U.S. Provisional Patent Application Ser. No. 61/536,981, entitled "Tissue Treatment Systems and Methods Having a Non-Tactile-Stimulus-Activated, Macroscopically-Deforming Material," filed Sep. 20, 2011, which is incorporated herein by reference for all purposes.

BACKGROUND OF THE INVENTION

1. Field of the Invention

The present invention relates generally to tissue treatment systems and more particularly to a reduced pressure tissue treatment system having a non-tactile-stimulus-activated, macroscopically-deforming material.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, a system for treating a tissue site of a patient is provided. The system includes a dressing filler adapted to be positioned at the tissue site. The dressing filler includes a base and a plurality of nodes extending from the base. The base further includes a plurality of openings disposed in the base. At least one of the plurality of nodes is comprised of a non-tactile-stimulus-activated, macroscopically-deforming (NTSAMD) material.

In another embodiment, a system for treating a tissue site of a patient includes a dressing filler adapted to be positioned at the tissue site. The dressing filter includes a plurality of nodes comprised of a non-tactile-stimulus-activated, macroscopically-deformed (NTSAMD) material.

In yet another embodiment, a system for treating a tissue site of a patient includes an open-cell, reticulated foam having a plurality of flow channels formed between cell struts. At least a portion of the cell struts are coated with a non-tactile-stimulus-activated, macroscopically-deformed (NTSAMD) material.

In still another embodiment, a method for treating a tissue site of a patient includes positioning a dressing filler in contact with the tissue site. The dressing filler includes having a plurality of nodes comprised of a non-tactile-stimulus-activated, macroscopically-deforming (NTSAMD) material. The method further includes supplying a stimulus to the plurality of nodes to cause deformation and movement of the nodes. The nodes are cell struts associated with an open-cell reticulated foam.

Other objects, features, and advantages of the illustrative embodiments will become apparent with reference to the drawings and detailed description that follow.

BRIEF DESCRIPTION OF THE DRAWINGS

FIG. 3 illustrates a cross-sectional front view of the dressing filler of FIG. 2 taken at 3-3;

FIG. 4 illustrates a cross-sectional front view of the dressing filler of FIG. 3, the dressing filler being illustrated in an active state;

FIG. 5 illustrates a cross-sectional front view of a dressing filler according to an illustrative embodiment, the dressing filler being illustrated in an active state;

FIGS. 6A and 6B illustrate a cross-sectional front view of a dressing filler according to an illustrative embodiment;

FIG. 7 illustrates a cross-sectional front view of a dressing filler according to an illustrative embodiment;

DETAILED DESCRIPTION OF ILLUSTRATIVE EMBODIMENTS

Figure 1:
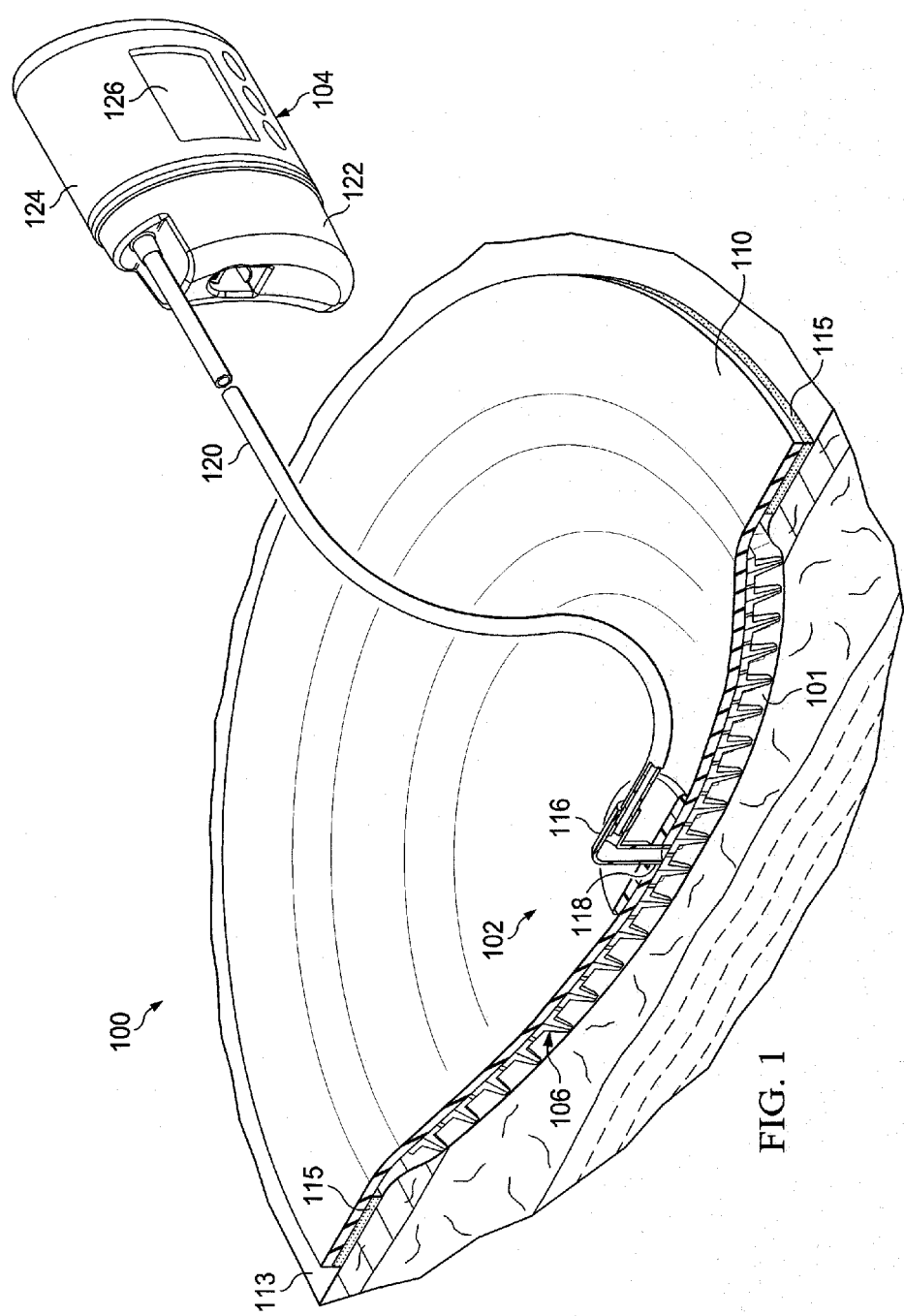
FIG. 1 illustrates a partially cross-sectional, perspective view of a tissue treatment system according to an illustrative embodiment.
Figure 2:
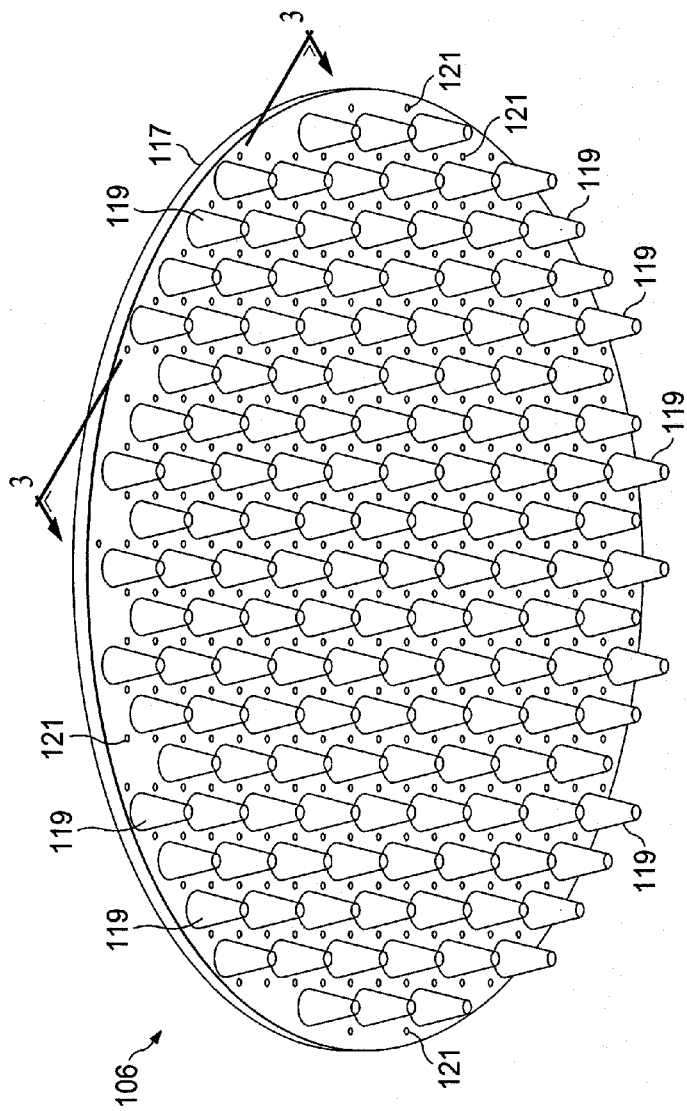
FIG. 2 illustrates a perspective view of a dressing filler of the tissue treatment system of FIG. 1.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The tissue treatment systems and methods described herein improve the treatment of a tissue site by providing a non-tactile-stimulus-activated, macroscopically deforming (NT-SAMD) material in proximity to or in contact with the tissue site. The NTSAMD material is a material that is capable of changing states or shapes in the presence of a stimulus. More specifically, the NTSAMD material is capable of undergoing mechanical deformation in the presence of the stimulus. The NTSAMD material is characterized as being non-tactile since the stimulus being provided is non-tactile in nature. In other words, the mechanical deformation is not caused by the tactile or direct application of a force by a user to the NTSAMD material. Instead, the stimulus supplied to the NTSAMD material may be, for example, a visible light stimulus. In one illustrative embodiment, the exposure of the NTSAMD material to a visible light stimulus of a particular wavelength causes the NTSAMD material to undergo macroscopic mechanical deformation. When the NTSAMD material is positioned near the tissue site, this deformation is capable of changing the profile of microstrain at the tissue site such that a more even distribution of new granulation tissue is developed. In addition, the resulting movement of the NTSAMD material may be helpful in discouraging adhesion between the NTSAMD material and the tissue site, thereby simplifying the process of removing dressings incorporating the NTSAMD material from the tissue site.

While additional examples of NTSAMD materials are provided herein, the NTSAMD material may be a shape-memory polymer that is able to actively change from a first shape to a second shape. The first shape of a shape-memory polymer is a temporary shape that is obtained by mechanical deformation of the polymer and fixation of that deformation. The second shape is a permanent shape, which may be achieved by applying the non-tactile stimulus to the polymer.

Referring to FIGS. 1-4, an illustrative embodiment of a tissue treatment system 100 for treating a tissue site 101 on a patient includes a dressing 102 placed proximate to the tissue site 101 and a therapy unit 104 fluidly coupled to the dressing 102. As used herein, the term "tissue site" may refer to a wound, such as a wound, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 102 is configured to promote the growth of new tissue at the tissue site 101 and includes a dressing filler 106 positioned adjacent to or, in some embodiments, in contact with the tissue site 101. The dressing 102 may further include a cover or drape 110 positioned over the dressing filler 106 to secure the dressing filler 106 at the tissue site 101 and to seal a space that is located beneath the cover and that is at least partially occupied by the dressing filler 106. In one embodiment, the drape 110 extends beyond a perimeter of the tissue site 101 and is placed either in contact with or otherwise in proximity to a patient's epidermis 113 to create a fluid seal between the drape 110 and the epidermis 113. The drape 110 may include an adhesive 115 or bonding agent to secure the drape 110 to the epidermis 113. In one embodiment, the adhesive 115 may be used to create a seal between the drape 110 and the epidermis 113 to prevent leakage of reduced pressure from the tissue site 101. In another embodiment, a seal layer (not shown) such as, for example, a hydrogel or other material may be disposed between the drape 110 and the epidermis 113 to augment or substitute for the sealing properties of the adhesive 115. As used herein, "fluid seal" means a seal adequate to maintain reduced pressure at a desired site given the particular reduced pressure source involved and the particular treatment desired. In one embodiment, the drape 110 and the bonding characteristics of the drape 110 provide sealing sufficient to prevent leakage greater than 0.5 L/min at 125 mmHg reduced pressure.

The dressing 102 further may include a reduced pressure adapter 116 fluidly coupled to the space beneath the cover 110. In one embodiment, the interface 116 may be positioned adjacent to or coupled to the cover 110 to provide fluid access to the dressing filler 106 and the tissue site 101. The drape 110 includes an aperture 118 for providing fluid access to the interface 116. A conduit 120 fluidly couples the therapy unit 104 and the interface 116. The interface 116 is capable of delivering reduced pressure to the tissue site 101.

In one embodiment, the therapy unit 104 includes a fluid containment member 122 in fluid communication with a reduced pressure source 124. In the embodiment illustrated in FIG. 1, the fluid containment member 122 is a collection canister that includes a chamber for collecting fluids from the tissue site 101. The fluid containment member 122 alternatively could be an absorbent material or any other container, device, or material that is capable of collecting fluid.

The conduit 120 may be a multi-lumen tube that is capable of providing one or more conduits to deliver reduced pressure to the dressing 102 and one or more conduits to sense the amount of pressure at the tissue site 101. Liquids or exudates communicated from the dressing filler 106 through the conduit 120 are removed from the conduit 120 and retained within the collection canister 122.

Referring still to FIG. 1, the reduced pressure source 124 may an electrically-driven vacuum pump. In another implementation, the reduced pressure source 124 may instead be a manually-actuated or manually-charged pump that does not require electrical power. In one embodiment, the reduced pressure source 124 may be one or more piezoelectric-actuated micropumps that may be positioned remotely from the dressing 102, or at the dressing beneath or adjacent to the cover 110. The reduced pressure source 124 instead may be any other type of pump, or alternatively a wall suction port or air delivery port such as those available in hospitals and other medical facilities. The reduced pressure source 124 may be housed within or used in conjunction with the therapy unit 104, which may also contain sensors, processing units, alarm indicators, memory, databases, software, display units, and user interfaces 126 that further facilitate the application of reduced pressure treatment to the tissue site 101. In one example, pressure-detection sensors (not shown) may be disposed at or near the reduced pressure source 124. The pressure-detection sensors may receive pressure data from the interface 116 via lumens in the conduit 120 that are dedicated to delivering reduced pressure data to the pressure-detection sensors. The pressure-detection sensors may communicate with a processing unit that monitors and controls the reduced pressure that is delivered by the reduced pressure source 124.

In the embodiment illustrated in FIGS. 1-4, the dressing filler 106 includes a base 117 and a plurality of nodes 119 or projections extending from the base 117. The dressing filler 106 further includes a plurality of openings 121 disposed in the base 117, the openings 121 preferably being located between the nodes 119. The base 117 may be a medical-grade, silicone-based material or any other biocompatible flexible material. Other suitable examples of materials may include plasticized PVC (PPVC), thermoplastic elastomers (TPE), thermoplastic polyurethane (TPU), and foamed versions of these and other foamed polymers such as polyolefins, polyamides, and polyesters. As described in more detail herein, at least one of the plurality of nodes 119 is comprised of the NTSAMD material. In one embodiment, each of the plurality of nodes 119 is comprised of the NTSAMD material. Furthermore, the nodes may be comprised of two or more different NTSAMD materials.

As previously described, the NTSAMD material may be any material that is capable of macroscopically deforming in the presence of a non-tactile stimulus. In one embodiment, the NTSAMD material is a photo- or light-activated polymer. The light-activated polymer is capable of undergoing macroscopic deformation when irradiated by light at particular wavelengths. The polymer is "activated" by the light, which promotes photochemical reactions that alter the structure of the crosslinked polymer network. These structural alterations result in the macroscopic deformation of the material. The response may be described as photomechanical in nature, but the underlying mechanisms that drive the response may be mechanically, chemically, or thermally driven. The various forms of energy used to activate the light-activated polymer may include visible and non-visible light, or other forms of electromagnetic radiation.

Examples of suitable light-activated polymers include, without limitation, polyvinylidene fluoride (PVDF), or alternatively polymers incorporating cinnamic acid (CA) or cinnamylidene acetic acid (CAA) moieties. The CA or CAA act as light-activated switches that have been incorporated into a polymer architecture. In one embodiment, the CA molecules are grafted to a copolymer of n-butylacrylate, hydroxyethyl methacrylate, ethylenegylcol-1-acrylate-2-CA, and poly(propylene glycol)-dimethacrylate ($M_n$=560 gmol$^{-1}$) as the cross-linker. In another embodiment, a polymer made from butylacrylate and 3 wt. % poly(propylene glycol)-dimethylacrylate ($M_n$=1000 gmol$^{-1}$) as a cross-linker, with 20 wt. % star-poly(ethylene glycol) end capped with terminal CAA groups. Each of the above-mentioned polymers has a permanent shape determined by its cross-links, but a temporary shape may be obtained by stretching the polymers. Subsequent irradiation of the polymers by ultraviolet (UV) light having a wavelength greater than 260 nm creates new covalent bonds that fix the temporary shape. A return to the permanent shape may be realized by exposing the polymers to UV light at wavelengths less than 260 nm, which cleaves the cross-links associated with the temporary shape. This example as well as other examples of suitable polymers may be found in *Shape-Memory Polymers* (Behl, Marc and Andreas Lendlein, Materials Today, vol. 10, no. 4, April 2007).

In another embodiment, a light-activated polymer may include an epoxy based formulation of a water soluble amine such as Jeffamine® polyetheramines and polyethylene glycol or EGDE in an aqueous solution that is combined with a light-emitting dopant, dye or photo initiator such as methylene blue. The initial aqueous solution in the dye is suspended or polymerized into the epoxy. After the curing process is complete, the polymer is hydrated and swollen with aqueous solution and photo irradiation of the material, which creates a pH change within the hydrated polymer to acid. The acids swell the amines further, and the amount of swelling is tunable by changing ratios and concentrations of the epoxy components and the dye. When the irradiation is stopped, the reaction stops and the polymer relaxes back to its neutral hydrated state, thereby creating an effective photo switch mechanism for a light-activated polymer.

To further refine or reverse the switching mechanism, a chelator or quenching molecule can be used to reverse or rebalance the polymer at a different wavelength of light. An example of this is the use of titanium dioxide in the polymer to oxidize the aqueous solution. When irradiated it produces oxygen, which can then quench the fluorescence of a dye such as a tris(4,7-diphenyl-1,10-phenanthroline)ruthenium(II) bis (hexafluorophosphate) complex. There are many additional chemicals and compound molecules that may be used for the switching process such as functionalized dendrimers with amino or other surface groups, chemiluminescent dyes, laser dyes, photochromic dyes, phthalocyanines, porphyrins, fluoropolymers and monomers. This method is also applicable to changing the polymer ions selectivity, allowing the control of the polymers hydrophilic and hydrophobic properties in order to control the polymer swelling.

The above-mentioned examples and other examples of light-activated polymers are included in U.S. Pat. No. 7,859, 168, which is hereby incorporated by reference.

While a light-activated polymer may be an excellent NTSAMD material, in another embodiment the NTSAMD material may be a piezoelectric material. The piezoelectric material is a material that macroscopically deforms when an electric current is passed through the material. Examples of suitable piezoelectric materials include, without limitation, PVDF.

Another suitable NTSAMD material may include a thermally-activated polymer that undergoes macroscopic deformation when exposed to a temperature change. Examples of suitable thermally-activated polymers include, without limitation, polystyrene or other vinyl polymer crosslinked with divinyl benzene, bis(4-(vinyloxy)butyl)terephthalate or bis (4-((vinyloxy)methyl)cyclohexyl)methyl terephthalate. This material and other examples are included in U.S. Pat. No. 6,759,481, which is hereby incorporated by reference.

The NTSAMD material undergoes macroscopic deformation in the presence of a non-tactile stimulus. The non-tactile stimulus, as described above, may be provided by light, electricity, heat (or absence of heat), or other stimuli that do not involve the application of an external force by a user to the material, either directly or indirectly. For example, the stimulus causing the deformation is not due to the user pressing on the material or other component of the dressing to activate the deformation properties of the material. Similarly, the NTSAMD material is one that does not require the user to apply a weight or other mechanical-force-supplying device, automatic or manual, to the NTSAMD material or other dressing components. While micro-mechanical forces may be involved in causing the macroscopic deformation, these micro-mechanical forces are activated by stimuli other than tactile actions of the user.

Macroscopic deformation of a material in response to being exposed to any non-tactile stimulus (either those described above—light, electricity, or heat—or any other stimulus) allows the material to create beneficial microstrain at the tissue site when the material is incorporated into a dressing as described herein. While the amount of deformation that occurs may vary for a given material and may vary based on the type, intensity, or amount of stimulus applied, in one embodiment, macroscopic deformation is deformation greater than or equal to about one percent (1%). The material primarily changes in dimensions in one direction or plane only; however, some minor dimensional change may occur in other directions or planes.

Referring still to FIGS. 1-4, each node 119 of the plurality of nodes that includes the NTSAMD material may be in the form of a unimorph. The unimorph configuration of a node 119 includes one NTSAMD material and a non-NTSAMD material. The non-NTSAMD material may be a medical-grade silicone-based material, or may be any other flexible biocompatible material.

The NTSAMD material is included in an active portion 123 of the node due to the ability of the NTSAMD material to deform in the presence of a non-tactile-stimulus. The non-NTSAMD material is included in an inactive portion 125 of the node 119 since the inactive portion will not deform in the presence of the non-tactile-stimulus. The active portion 123 and inactive portion 125 are joined together, such as by bonding, welding or other mechanical processes, or are otherwise formed together, such as by co-molding or co-extrusion processes. In one embodiment, the arrangement of the active portion 123 and the inactive portion 125 is symmetrical about an axis of symmetry 127 that bisects the node 119 in the view illustrated in FIG. 3. The node 119 in the unimorph configuration allows selective or controlled movement of the node to change the microstrain profile imparted to the tissue site 101 by the dressing filler 106. In other words, movement of the nodes 119 permits the location at which microstrain is applied to the wound by each node to be changed. This change in the microstrain profile allows a more uniform development of new tissue growth at the tissue site 101.

The dressing filler 106 is illustrated in FIG. 3 in an inactive state in which the nodes 119 are relaxed. Movement of the nodes 119 is accomplished by exposing the nodes 119 to a stimulus provided by a stimulus source 131. FIG. 4 illustrates an active state of the dressing filler 106 and nodes 119 in which the nodes 119, under the influence of the stimulus have moved from the original position of the nodes 119 in the inactive state (see FIG. 3). In one embodiment, the presence of the applied stimulus causes the NTSAMD material of the active portion 123 to deform by lengthening in a direction parallel to the axis of the symmetry 127. Since the inactive portion 125 of the nodes does not deform in the presence of the stimulus, the lengthening of the active portion 123 results in movement of the nodes as indicated in FIG. 4 by arrows 133. In the configuration illustrated in FIGS. 3 and 4, a pair 137 of complimentary nodes includes adjacent or continuous active portions 123 between the complimentary nodes. In this particular configuration, the inactive portion 125 of a particular node in a pair 137 is adjacent to or continuous with the inactive portion 125 of a node in an adjacent pair 137. This configuration of the active and inactive portions results in the nodes in each pair 137 of complimentary nodes moving toward one another as illustrated in FIG. 4 when stimulated.

FIG. 5 illustrates an alternative configuration of the nodes 119 of dressing filler 106 in the active state. In this configuration, the active portion 123 and inactive portion 125 of each node 119 is arranged such that across each column of nodes (a portion of one column being shown in FIG. 5) the active portion 123 and inactive portions 125 alternate. In other words, each node 119 includes an active portion 123 that is adjacent the inactive portion 125 of another node 119. Similarly, each node 119 includes an inactive portion 125 that is adjacent the active portion 123 of another node 119. This configuration of alternating active and inactive portions results in the nodes 119 moving in the same direction as indicated in FIG. 5 by arrows 141.

In either of the nodal configurations of FIGS. 4 and 5, the deformation of the active portion 123 as a result of applying the stimulus creates movement in the node 119 since the inactive portion 125 does not deform. Again, these configurations employing both an active portion and an inactive portion in a single node may be referred to as unimorphs. In one embodiment, the NTSAMD material, or alternatively the material comprising the inactive portion 125, may include plastically deformable or irreversible characteristics. When the node 119 enters an active state and moves to a position similar to those illustrated in FIGS. 4 and 5, such an irreversible material may cause the node 119 to undertake a permanent set after being deformed by the action of the NTSAMD material. In other words, the nodes 119 may be stimulated to move to the position associated with the active state and may not revert back to the original position associated with the inactive state when the stimulus is removed. In another embodiment, the materials associated with the node 119 may be elastically deformable and reversible throughout the expected range of motion associated with the node 119, thereby allowing the nodes 119 to revert to the original position associated with the inactive state in the absence of the stimulus.

In addition to the unimorph configurations described above, bimorph configurations employing two or more NTSAMD materials in a single node may be used in some embodiments. While not illustrated specifically, the bimorph configuration may be similarly represented by the illustrations associated with FIGS. 3-5. Instead of the nodes 119 of the dressing filler 106 having an active portion 123 and an inactive portion 125, the nodes 119 of the bimorph configuration include two or more active portions, each with a NTSAMD material. In one embodiment, the two or more NTSAMD materials each respond to a different stimulus. For example, two NTSAMD materials may be included in each node. One of these NTSAMD materials may be stimulated by light of a first wavelength, while the other NTSAMD material is stimulated by light of a second wavelength. Alternatively, the type of stimulus that activates each NTSAMD material may be different. For example, light of a particular wavelength may stimulate one of the NTSAMD materials, while the other NTSAMD material is stimulated by an electrical stimulus.

The bimorph configuration is capable of having plastically deformable or irreversible materials with each node 119 such that the stimulation of one of the NTSAMD materials results in irreversible movement of the node 119. However, it is also possible and even more desirable with this particular configuration to use materials that allow elastic deformation and movement of the nodes 119. In this manner, the nodes 119 may return to a non-stimulated, inactive state following stimulation. Further, unlike the nodes 119 of the unimorph configuration, the nodes of the bimorph configuration are capable of actively moving into two or more positions depending on the number of different NTSAMD materials present. For example, with reference to FIG. 4, a bimorph configuration of the nodes 119 in which the inactive portion 125 of each node 119 is replaced by a second NTSAMD material permits each node 119 to have two active states, and an inactive state similar to that illustrated in FIG. 3. To move to the first active state, the first NTSAMD material is stimulated, and the nodes 119 move in similar directions to those indicated by arrows 133 in FIG. 4. To move to a second active state, the first stimulus is removed and a second stimulus applied. In the second active state, the first NTSAMD material is no longer deformed, and instead the second NTSAMD material is stimulated and deforms. This deformation of the second NTSAMD material results in movement of the nodes 119 in a direction opposite to the arrows 133 illustrated in FIG. 4.

The positioning of the NTSAMD materials in the bimorph configuration may be varied to obtain the desired movements of the nodes 119. For example, with reference to FIG. 5, if the first NTSAMD material of the bimorph configuration occupies a portion of the node similar to the active portion 123, and the second NTSAMD material occupies a portion of the node similar to the inactive portion 125, the movement of the nodes to the first active state (i.e. in which only the first NTSAMD material is stimulated) is similar to that illustrated in FIG. 5. In the second active state, the second NTSAMD material is stimulated, and the nodes move in a direction opposite to the arrows 141 illustrated in FIG. 5.

In still another embodiment, the nodes 119 of the dressing filler 106 may be comprised of a single NTSAMD material without any other NTSAMD material or any inactive portion. This "uniform" configuration of the nodes also allows an active state in which the NTSAMD is exposed to a stimulus and an inactive state in which no stimulus is applied. Applying a stimulus to the uniform node 119 causes the NTSAMD to deform and lengthen in a direction extending away from the base 117 of the dressing filler 106. Since the dressing filler 106 is secured at the tissue site 101 by a cover 110, the stimulation and lengthening of the node 119 increases the microstrain experienced by the tissue site 101.

Referring again to FIGS. 1-4, the type of nodes 119 positioned on the base 117 may vary. In other words, a particular dressing filler 106 may include a mixture of unimorph-, bimorph- and uniform-configured nodes. Alternatively, all of the nodes 119 on a particular dressing filler 106 may be similarly configured. If unimorph or bimorph configurations are used, the positioning of the NTSAMD materials or inactive portions 125 could be either as illustrated in FIG. 4 or FIG. 5, or alternatively other configurations may be employed to change the directional movement of the nodes when exposed to the stimulus. While FIGS. 4 and 5 illustrate only a two-dimensional representation of a row of nodes 119, the nodes 119 may be arranged on the base 117 in orthogonal rows and columns or alternatively in a pattern of rings of increasing diameter. Any other suitable arrangement of the nodes 119 on the base 117 made be employed, including random positioning of the nodes 119. Finally, it should also be noted that while the illustrated nodes 119 are tapered cylinders, the nodes may instead be non-tapered cylinders, semispherical, rectangular, pyramidal, or any other suitable shape.

The stimulus source 131 used to activate the NTSAMD materials described herein may vary depending on the particular NTSAMD material chosen. In one embodiment, where the NTSAMD material is a light-activated polymer, the stimulus source 131 may be a light source positioned external to the dressing 102 to direct light toward the dressing 102. In this embodiment, the cover 110 and the base 117 may be transparent to the particular wave lengths of light generated by the stimulus source 131 such that the NTSAMD is exposed to the light. The light source may be a light emitting diode (LED) associated with control circuitry and a power source. An example of one particular stimulus source 131 includes an infrared light source that is capable of producing light in the infrared spectrum (400 nm to 1550 nm wavelength).

While a light source external to the dressing 102 may be useful when transparent materials are used, other configurations may be provided for delivering the light to the NTSAMD material. In one embodiment, light guides may be provided adjacent to or integrated within the dressing filler 106 to deliver light from the light source to the NTSAMD material. The light guides may be fiber optic tubing, or alternatively, a light-transmitting coating positioned on the cover 110 or the dressing filler 106. Suitable coatings may include polymethyl pentene, polyacrylics and polyacrylates, polyurethanes, cyclic olefin copolymers, polyesters, or any light transparent polymer such as for example acrylics.

Referring to FIG. 6A, a light-transmitting coating 641 is positioned on the dressing filler 106. The thickness of the of light-transmitting coating 641 is exaggerated in FIG. 6A in order to better illustrate the path of light (represented by line 643) as the light enters the light-transmitting coating 641 from the top of the dressing filler 106. The light reflects internally within the light-transmitting coating 641 such that light is delivered to the NTSAMD material.

In still another embodiment, the light source may be positioned internal to the dressing beneath the cover 110. In one example, a light emitting diode (LED) and associated circuitry may be positioned beneath the cover 110.

In yet another embodiment illustrated in FIG. 6B, a coating 645 may be applied to the dressing filler 106 that includes a light-emitting polymer. The light-emitting polymer is capable of emitting a light that is capable of stimulating the NTSAMD material. Examples of the light-emitting polymer include, without limitation, poly(p-phenylene vinylene (PPV) & poly(9,9'-dioctylfluorene)) offered by Cambridge Display Technology. Other polymer (organic) light emitting diodes (P-OLEDs) may also be used. These polymers may be controlled electrically and may provide either a constant or intermittent (i.e. pulsed) source of light.

When NTSAMD materials are used that accept non-light stimuli, the stimulus source 131 is chosen to provide the necessary stimulus. For example, when a piezoelectric NTSAMD is incorporated into the dressing filler 106, the stimulus source 131 may be a source of electric current such as a battery or other power source. Like the light source, the electric current source may be associated with certain control electronics that are capable of controlling the delivery of the stimulus to the NTSAMD material.

In one particular example of a tissue treatment system similar to tissue treatment system 100 of FIG. 1, electrical wires may be embedded within the conduit 120 to provide electrical signals between the therapy unit 104 and a light-emitting device integrated into or placed proximate the interface 116. The dressing filler 106 includes nodes having NTSAMD material, and the dressing filler is coated with a light-transmitting or clear polymer. Additionally, the base 117 of the dressing filler 106 is preferably clear and able to transmit light. Electrical signals generated at the therapy unit 104 travel to the light-emitting device causing light to be generated. This light is then transmitted through the base 117 and through the light-transmitting coating to the NTSAMD material at the nodes. Each light-activated nodes then bends, twists, or otherwise deforms in an amount equal to at least 100% of the thickness of the node.

Referring to FIG. 7, a dressing filler 706 according to an illustrative embodiment includes a base 717 and a plurality of nodes 719. The dressing filler 706 may be similar in construction and shape to dressing filler 106. A plurality of openings 721 are positioned in the base 717 to allow communication between opposing sides of the base 717. Unlike dressing filler 106, the nodes 719 of dressing filler 706 are not molded or otherwise formed from the NTSAMD material. Instead, the dressing filler 706 includes one or more coatings 747 that are applied to the nodes 719. In FIG. 7, the one or more coatings include a first coating 747a and a second coating 747b. The first coating 747a includes a first NTSAMD material, and the second coating 747b includes a second NTSAMD material. By positioning different NTSAMD materials on opposing sides of each node, a similar movement of the nodes 719 may be obtained as the movements described previously for the bimorph configuration of nodes 119. In the embodiment illustrated in FIG. 7, the coatings 747a, 747b are arranged similar to the arrangement of the active and inactive portions in FIG. 4 such that complimentary nodes 737 are capable of moving toward one another or away from one another. Alternatively, the coatings 747a, 747b may be arranged on each node 719 similar to the active and inactive portions in FIG. 5 such that the nodes 719 move together in one direction or another.

The configuration of nodes 719 shown in FIG. 7 is similar to the bimorph configuration of nodes 119 since two NTSAMD materials are associated with the nodes 119. In another embodiment, one or more of the nodes 719 may include a coating having a single NTSAMD material applied to only a portion of the node 719. This configuration is similar to the unimorph configuration described for nodes 119 since only a portion of the node 719 actively deforms in the presence of the stimulus. Alternatively, the nodes 719 may be uniformly coated with only a single NTSAMD material, which is functionally analogous to the uniform configuration described for nodes 119.

Figure 8:
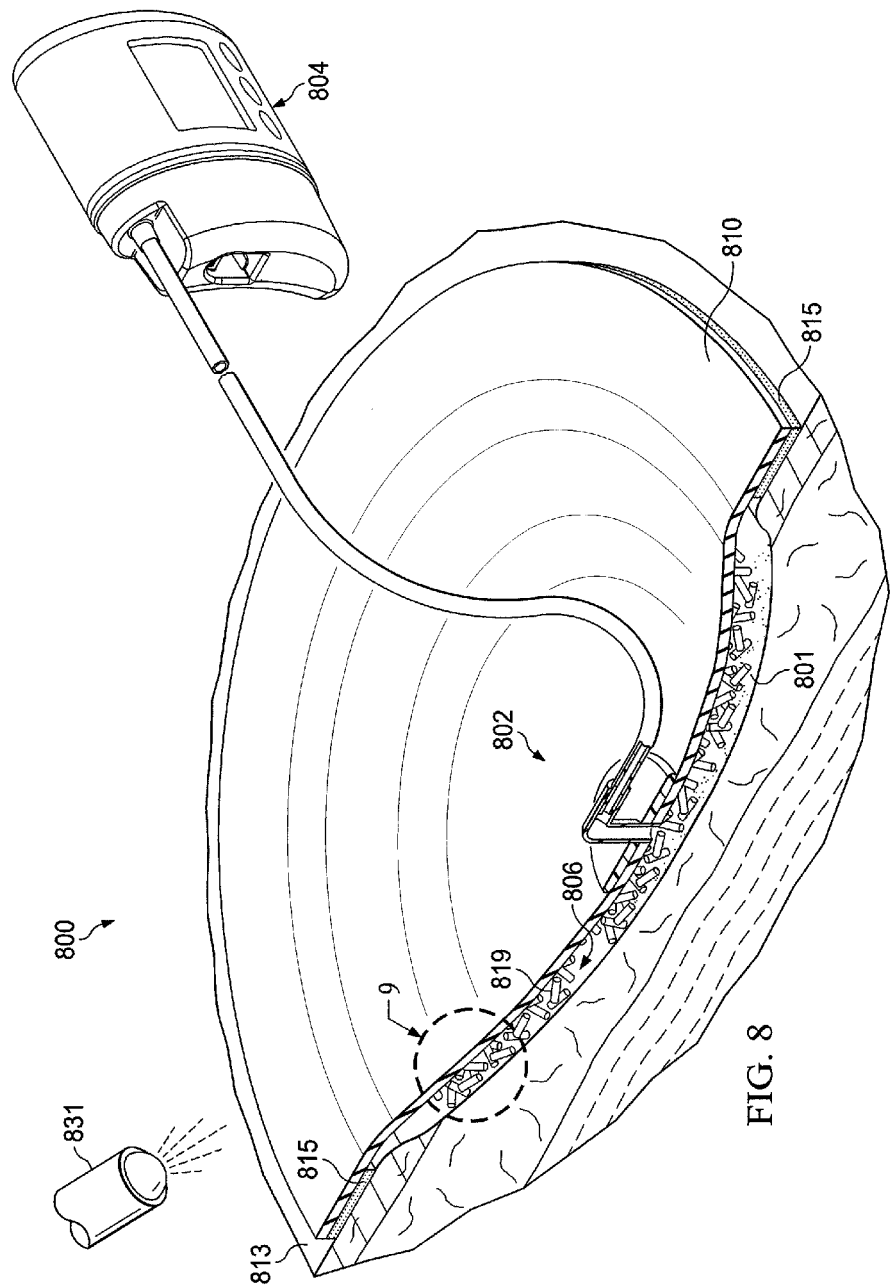
FIG. 8 illustrates a partially cross-sectional, perspective view of a tissue treatment system according to an illustrative embodiment.
Figure 9:
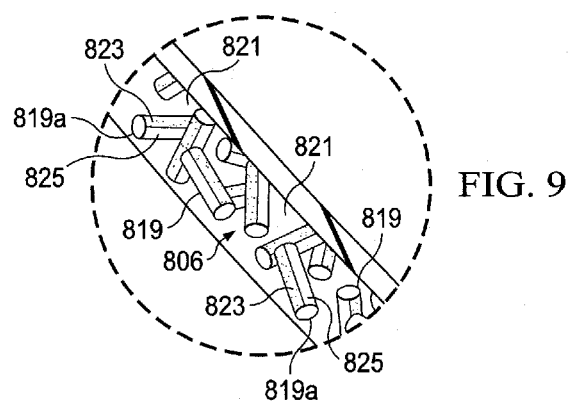
FIG. 9 illustrates a front view of a dressing filler of the tissue treatment system of FIG. 8 represented at Detail 9.

Referring to FIGS. 8 and 9, an illustrative embodiment of a tissue treatment system 800 for treating a tissue site 801 on a patient includes a dressing 802 placed proximate to the tissue site 801 and a therapy unit 804 fluidly coupled to the dressing 802. The dressing 802 is configured to promote the growth of new tissue at the tissue site 801 and includes a dressing filler 806 positioned adjacent to or, in some embodiments, in contact with the tissue site 801. The dressing 802 may further include a cover or drape 810 positioned over the dressing filler 806 to secure the dressing filler 806 at the tissue site 801 and to seal a space that is located beneath the cover and that is at least partially occupied by the dressing filler 806. In one embodiment, the drape 810 extends beyond a perimeter of the tissue site 801 and is placed either in contact with or otherwise in proximity to a patient's epidermis 813 to create a fluid seal between the drape 810 and the epidermis 813. The drape 810 may include an adhesive 815 or bonding agent to secure the drape 810 to the epidermis 813. In one embodiment, the adhesive 815 may be used to create a seal between the drape 810 and the epidermis 813 to prevent leakage of reduced pressure from the tissue site 801. In another embodiment, a seal layer (not shown) such as, for example, a hydrogel or other material may be disposed between the drape 810 and the epidermis 813 to augment or substitute for the sealing properties of the adhesive 815.

The dressing filler 806 includes a plurality of nodes 819. Unlike dressing filler 106, the nodes 819 of dressing filler 806 are not connected to or otherwise molded or formed with a base. Instead, the nodes 819 are individual, unconnected items that are positioned at the tissue site 801 beneath the drape 810. As illustrated in FIG. 9, preferably the random positioning of the nodes 819 is such that spaces 821 between the nodes 819 allow adequate distribution of reduced pressure. The ability of the dressing filler 806 to manifold reduced pressure may be aided by the shape or size of the nodes. In FIGS. 8 and 9, the nodes are rectangular cubical in shape, but alternatively, the nodes 819 could be spherical, cylindrical, cubical, or any other particular shape. While the nodes 819 illustrated are the same size and shape, variations in size and shape among the individual nodes 819 may aid in distribution of reduced pressure due to the increased presence of spaces 821 between nodes.

Like the nodes 119 of FIGS. 1-4, nodes 819 provide point loads and thus create microstrain at the tissue site 801 when the sealed space beneath the drape 810 is supplied with reduced pressure. Each node 819 may include one or more NTSAMD materials to promote the movement of the nodes 819 similar to the movements described previously with reference to nodes 119. The nodes 819 included in dressing filler 806 may be unimorph-, bimorph-, or uniform-configured as previously described. For example, a unimorph-configured node 819a includes an active portion 823 and an inactive portion 825. The active portion 823 includes a NTSAMD material capable of deformation in the presence of a stimulus provided by a stimulus source 831. The inactive portion 825 is formed from or otherwise comprises a material that does not actively deform in the presence of the stimulus.

When the stimulus is applied to dressing filler 806, the movement of nodes 819 permits a spatial redistribution of the point loads applied by the nodes 819 to the tissue site 801. This in turn creates a different microstrain profile (i.e. the distribution of microstrain) at the tissue site 801, thereby aiding in the even development of granulation tissue and preventing the adhesion of new tissue growth to the dressing filler 806.

Figure 11:
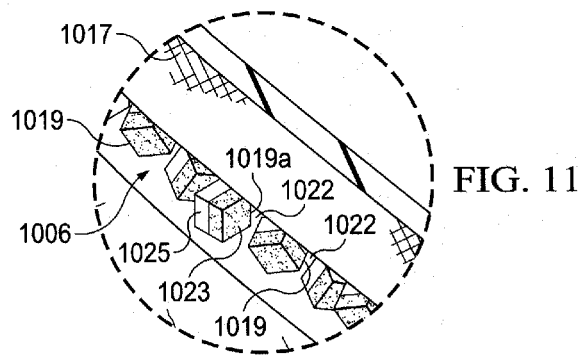
FIG. 11 illustrates a front view of a dressing filler of the tissue treatment system of FIG. 10 represented at Detail 11.
Figure 10:
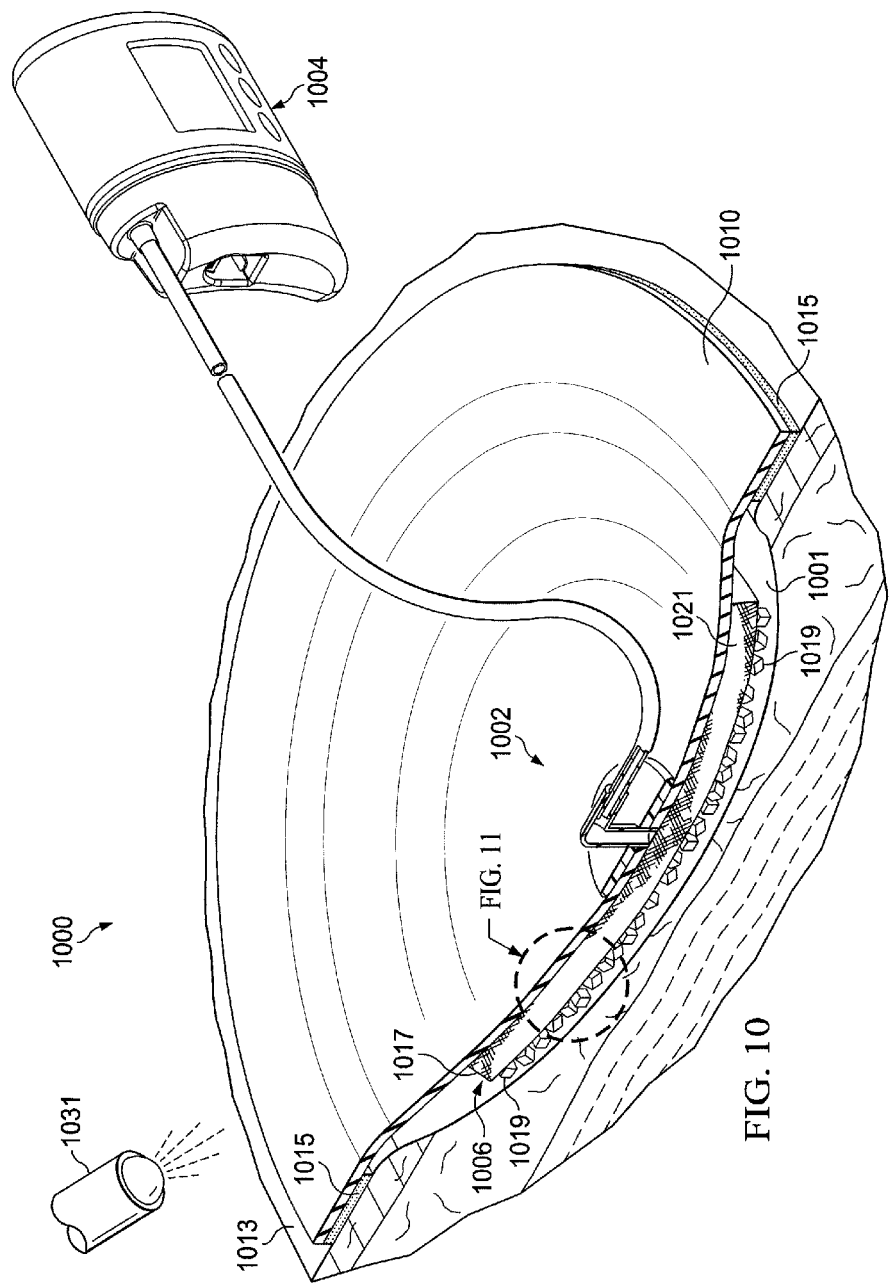
FIG. 10 illustrates a partially cross-sectional, perspective view of a tissue treatment system according to an illustrative embodiment.

Referring to FIGS. 10 and 11, an illustrative embodiment of a tissue treatment system 1000 for treating a tissue site 1001 on a patient includes a dressing 1002 placed proximate to the tissue site 1001 and a therapy unit 1004 fluidly coupled to the dressing 1002. The dressing 1002 is configured to promote the growth of new tissue at the tissue site 1001 and includes a dressing filler 1006 positioned adjacent to or, in some embodiments, in contact with the tissue site 1001. The dressing 1002 may further include a cover or drape 1010 positioned over the dressing filler 1006 to secure the dressing filler 1006 at the tissue site 1001 and to seal a space that is located beneath the cover and is at least partially occupied by the dressing filler 1006. In one embodiment, the drape 1010 extends beyond a perimeter of the tissue site 1001 and is placed either in contact with or otherwise in proximity to a patient's epidermis 1013 to create a fluid seal between the drape 1010 and the epidermis 1013. The drape 1010 may include an adhesive 1015 or bonding agent to secure the drape 1010 to the epidermis 1013. In one embodiment, the adhesive 1015 may be used to create a seal between the drape 1010 and the epidermis 1013 to prevent leakage of reduced pressure from the tissue site 1001. In another embodiment, a seal layer (not shown) such as, for example, a hydrogel or other material may be disposed between the drape 1010 and the epidermis 1013 to augment or substitute for the sealing properties of the adhesive 1015.

The dressing filler 1006 includes a base 1017 and plurality of nodes 1019 or projections extending from the base 1017. In the embodiment illustrated in FIGS. 10 and 11, the base 1017 is a fibrous material having woven or non-woven fibers. The base 1017 may further include a plurality of openings 1021 that in one embodiment are apertures that are mechanically-formed in the fibrous material. Alternatively, the openings 1021 may be spaces that are present between fibers in the fibrous base 1017. If a woven fibrous material is used, the number of openings 1021 and the size of the openings 1021 may be controlled by the density of the weave. Regardless of how the openings 1021 are formed or otherwise provided, the openings 1021 permit better distribution of reduced pressure during treatment and easier flow of exudate and other fluids from the tissue site 1001 out of the sealed space.

Nodes 1019 are attached to or otherwise positioned on a surface of the base 1017. In one embodiment, the nodes 1019 may be adhesively secured or bonded to the base 1017. In another embodiment, the nodes may be thermally bonded to the base 1017. Any attachment method may be used to position the nodes 1019 on the base 1017. The nodes 1019 may be individual components that are positioned on the base 1017, or alternatively may be connected to other nodes 1019 prior to attaching the connected nodes 1019 to the base 1017. As illustrated in FIG. 11, in one embodiment, the random and individual positioning of the nodes 1019 is such that spaces 1022 between the nodes 1019 allow adequate distribution of reduced pressure between the fibrous base 1017 and the tissue site 1001. The nodes illustrated in FIGS. 10 and 11 are cubical or rectangular cubical in shape, but like all the nodes described herein, the nodes 1019 could be spherical, cylindrical, or any other particular shape. While the nodes 1019 illustrated are the same size and shape, variations in size and shape among the individual nodes 1019 may be desired in some embodiments.

Like the nodes 119 of FIGS. 1-4, nodes 1019 provide point loads and thus create microstrain at the tissue site 1001 when the sealed space beneath the drape 1010 is provided with reduced pressure. Each node 1019 may include one or more NTSAMD materials to promote the movement of the nodes 1019 similar to the movements described previously with reference to nodes 119. The nodes 1019 included in dressing filler 1006 may be unimorph-, bimorph-, or uniform-configured as previously described. For example, a unimorph-configured node 1019a includes an active portion 1023 and an inactive portion 1025. The active portion 1023 includes a NTSAMD material capable of deformation in the presence of a stimulus provided by stimulus source 1031. The inactive portion 1025 is formed from or otherwise comprises a material that does not actively deform in the presence of the stimulus.

When the stimulus is applied to dressing filler 1006, the movement of nodes 1019 permits a spatial redistribution of the point loads applied by the nodes 1019 to the tissue site 1001. This in turn creates a different microstrain profile (i.e. the distribution of microstrain) at the tissue site 1001, thereby aiding in the even development of granulation tissue and preventing the adhesion of new tissue growth to the dressing filler 1006.

Figure 13:
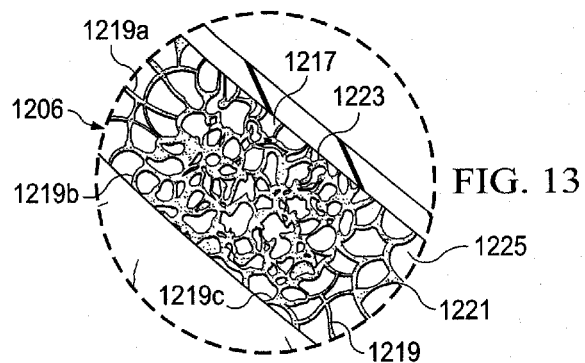
FIG. 13 illustrates a front view of a dressing filler of the tissue treatment system of FIG. 12 represented at Detail 13.
Figure 12:
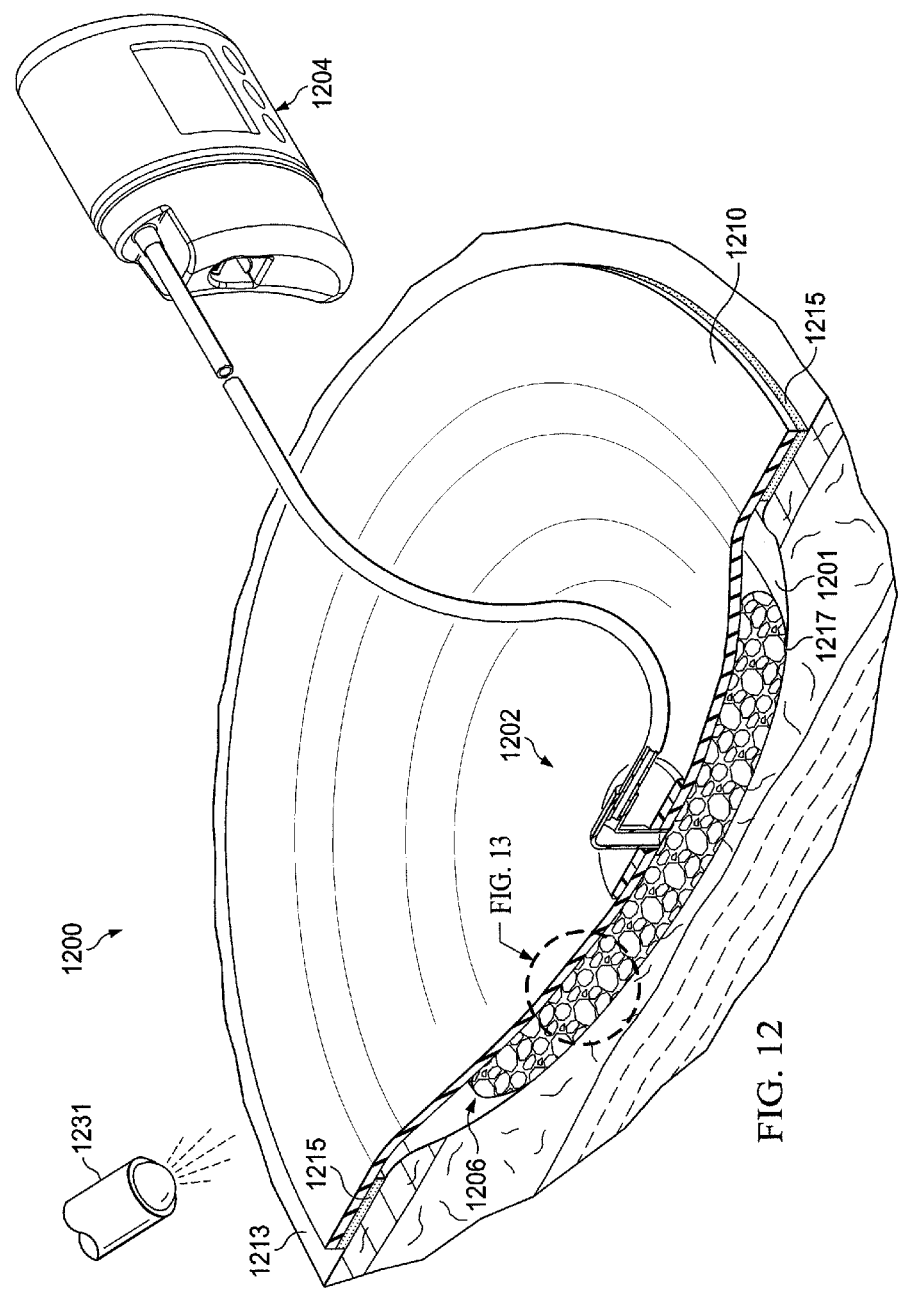
FIG. 12 illustrates a partially cross-sectional, perspective view of a tissue treatment system according to an illustrative embodiment.

Referring to FIGS. 12 and 13, an illustrative embodiment of a tissue treatment system 1200 for treating a tissue site 1201 on a patient includes a dressing 1202 placed proximate to the tissue site 1201 and a therapy unit 1204 fluidly coupled to the dressing 1202. The dressing 1202 is configured to promote the growth of new tissue at the tissue site 1201 and includes a dressing filler 1206 positioned adjacent to or, in some embodiments, in contact with the tissue site 1201. The dressing 1202 may further include a cover or drape 1210 positioned over the dressing filler 1206 to secure the dressing filler 1206 at the tissue site 1201 and to seal a space that is located beneath the cover and that is at least partially occupied by the dressing filler 1206. In one embodiment, the drape 1210 extends beyond a perimeter of the tissue site 1201 and is placed either in contact with or otherwise in proximity to a patient's epidermis 1213 to create a fluid seal between the drape 1210 and the epidermis 1213. The drape 1210 may include an adhesive 1215 or bonding agent to secure the drape 1210 to the epidermis 1213. In one embodiment, the adhesive 1215 may be used to create a seal between the drape 1210 and the epidermis 1213 to prevent leakage of reduced pressure from the tissue site 1201. In another embodiment, a seal layer (not shown) such as, for example, a hydrogel or other material may be disposed between the drape 1210 and the epidermis 1213 to augment or substitute for the sealing properties of the adhesive 1215.

The dressing filler 1206 includes an open-cell, reticulated foam 1217 that includes a plurality of flow channels 1221 formed between cell walls or struts 1219. The open-cell foam serves as a manifold to distribute reduced pressure to and remove fluids from the tissue site 1201. In one embodiment, the open-cell foam 1217 may be a polyurethane, open-cell, reticulated foam such as GranuFoam® material manufactured by Kinetic Concepts, Incorporated of San Antonio, Tex. Any material may be used as dressing filler 1206 provided that the material is capable of manifolding reduced pressure and providing structural elements that generate beneficial microstrain at the tissue site 1201 when reduced pressure treatment is applied. Besides cellular foams, porous tissue collections, liquids, gels, and foams that include, or cure to include, flow channels may be used.

The struts 1219 of the open-cell reticulated foam 1217 illustrated in FIGS. 12 and 13 provide the necessary structure for creating microstrain at the tissue site 1201 when reduced pressure treatment is provided. Like the nodes described herein, the struts 1219 may be formed from or coated with at least one NTSAMD material. The struts 1219 may be unimorph-, bimorph-, or uniform-configured as previously described. For example, a unimorph-configured strut 1219a may include an active portion 1223 that is coated with the NTSAMD material and an inactive portion 1225 that is not coated. Alternatively, a bimorph-configured strut 1219b may include two active portions, a first that includes a first NTSAMD material and a second that includes a second NTSAMD material. As another alternative, a uniform-configured strut 1219c may be provided in which the entire strut 1219c is coated with or formed from a single NTSAMD material.

During reduced pressure treatment, as reduced pressure is removed from the sealed space beneath drape 1210, the drape 1210 presses on the open-cell reticulated foam 1217 urging the foam 1217 toward the tissue site 1201. Some of the struts 1219 of the open-cell reticulated foam 1217 contact the tissue site 1201, and these struts 1219 provide a point load to the tissue site 1201 thereby creating a particular distribution of microstrain across the tissue site 1201. When a stimulus is provided by a stimulus source 1231 to the dressing filler 1206, the deformation of the NTSAMD material and movement of struts 1219 permits a spatial redistribution of the point loads applied by the struts 1219 to the tissue site 1201. This in turn creates a different microstrain profile (i.e. the distribution of microstrain) at the tissue site 1201 and helps prevent adhesion of new tissue growth to the dressing filler 1206.

The systems and methods described herein allow modification of the microstrain experienced by a tissue site without changing the dressing at the tissue site. In some cases, the microstrain modification involves simply a redistribution of the microstrain profile, while in other cases, the amplitude of the microstrain may be increased or decreased. The dressings described herein each incorporate nodes, struts, or other strain-inducing structures that include at least one NTSAMD material. The NTSAMD material, when stimulated by a non-tactile stimulus, undergoes macroscopic deformation which moves the strain-inducing structure associated with the dressing and therefore alters the microstrain experienced by the tissue site. Each of the dressings described herein is therefore believed to improve the treatment of a tissue site using reduced pressure tissue treatment, since changing the microstrain profile during reduced pressure treatment will result in more even formation of granulation tissue and will prevent adhesion of new tissue to the dressing.

While many of the systems described herein have been illustrated in use with tissue sites or wounds that are at or near the epidermis of a patient, the systems and methods may similarly be used to treat subcutaneous tissue sites, tunnel wounds, or other undermined areas of tissue.

It should be apparent from the foregoing that an invention having significant advantages has been provided. While the invention is shown in only a few of its forms, it is not just limited but is susceptible to various changes and modifications without departing from the spirit thereof.

We claim:

1. A dressing filler adapted to be positioned adjacent to a tissue site, the dressing filler comprising:
   a base;
   a plurality of nodes extending from the base, at least one of the nodes comprising a first portion and a second portion bisected by an axis of the at least one node, at least one of the first portion and the second portion comprising a non-tactile-stimulus-activated, macroscopically-deforming (NTSAMD) material, wherein the first portion is comprised of a first NTSAMD material and the second portion is comprised of a second different NTSAMD material; and
   a plurality of openings disposed in the base.

2. The dressing filler of claim 1, wherein the NTSAMD material is selected from the group consisting of:
   polyvinylidene fluoride (PVDF);
   a polymer incorporating cinnamic acid (CA);
   a polymer incorporating cinnamylidene acetic acid (CAA) moieties;
   an epoxy based formulation of a water soluble amine and polyethylene glycol in an aqueous solution that is combined with methylene blue; and
   a vinyl polymer crosslinked with divinyl benzene, bis(4-(vinyloxy)butyl)terephthalate or bis(4-((vinyloxy)methyl)cyclohexyl)methyl terephthalate.

3. The dressing filler of claim 1, wherein the NTSAMD material is a light-activated polymer.

4. The dressing filler of claim 1, wherein the NTSAMD material is a piezoelectric material.

5. The dressing filler of claim 1, wherein the NTSAMD material is a thermally-activated polymer.

6. The dressing filler of claim 1, wherein the first portion deforms in response to light of a first wavelength to provide movement of the at least one of the plurality of nodes in a first direction, and the second portion deforms in response to light of a second wavelength to provide movement of the at least one of the plurality of nodes in a second direction.

7. The dressing filler of claim 1, wherein the first portion comprises the NTSAMD material and the second portion comprises an inactive material.

8. The dressing filler of claim 7, wherein the first portion deforms in response to light of a particular wavelength, thereby providing movement of the at least one of the plurality of nodes.

9. The dressing filler of claim 1, wherein the at least one of the plurality of nodes is uniformly comprised of the NTSAMD material.

10. The dressing filler of claim 1, wherein:
    in response to a first stimulus, the first portion deforms more than the second portion, thereby resulting in movement of the at least one of the plurality of nodes in a first direction; and
    in response to a second stimulus, the second portion deforms more than the first portion, thereby resulting in movement of the at least one of the plurality of nodes in a second direction.

11. The dressing filler of claim 10, wherein the first direction is opposite to the second direction.

12. The dressing filler of claim 10, wherein at least one of the first and second stimulus is selected from the group consisting of:
    a light stimulus;
    an electrical stimulus; and
    a thermal stimulus.

13. The dressing filler of claim 1, wherein in response to a stimulus, the at least one of the plurality of nodes deforms in a direction substantially parallel to a longitudinal axis of the node.

14. The dressing filler of claim 13, wherein in the absence of the stimulus, the at least one of the plurality of nodes returns substantially to the shape and position of the node prior to application of the stimulus.

15. The dressing filler of claim 10, wherein the deformation of the first and second portions is reversible when the stimulus that caused the deformation is removed.

16. The dressing filler of claim 10, wherein the deformation of the first and second portions is irreversible when the stimulus that caused the deformation is removed.

17. The dressing filler of claim 1, wherein:
    the NTSAMD material is a light-activated polymer; and
    the dressing filler further comprises a light guide for providing light to the NTSAMD material.

18. The dressing filler of claim 17, wherein the light guide is a fiber optic tube.

19. The dressing filler of claim 17, wherein the light guide is a coating comprising a light-emitting polymer positioned on at least a portion of the dressing filler.

20. The dressing filler of claim 1, wherein at least one of the plurality of nodes has a shape selected from the group consisting of:
    a columnar shape; and
    a cone shape.

21. The dressing filler of claim 1, wherein the NTSAMD material is a coating on the at least one of the plurality of nodes.

22. The system of claim 1, wherein the nodes extending from the base are positioned toward the tissue site.

23. The dressing filler of claim 1, wherein the plurality of openings are located between the plurality of nodes.

24. The dressing filler of claim 1, wherein the plurality of openings are positioned to allow communication between opposing sides of the base.

25. The dressing filler of claim 1, wherein the first portion is positioned on an opposite side of the axis of the at least one node from the second portion.

26. The dressing filler of claim 1, wherein the first portion and the second portion are arranged symmetrical about the axis of the at least one node.

27. The dressing filler of claim 1, wherein the NTSAMD material is configured to macroscopically deform without a force being applied to the NTSAMD material.

\* \* \* \* \*